United States Patent [19]
Driscoll, Jr. et al.

[11] Patent Number: 5,993,389
[45] Date of Patent: Nov. 30, 1999

[54] DEVICES FOR PROVIDING ACOUSTIC HEMOSTASIS

[75] Inventors: Edward C. Driscoll, Jr., Portola Valley, Calif.; Lawrence A. Crum, Issaquah, Wash.; Wing K. Law, Mountain View; Stan DeMarta, Pleasanton, both of Calif.

[73] Assignee: THS International, Inc., Indianapolis, Ind.

[21] Appl. No.: 08/562,280

[22] Filed: Nov. 22, 1995

Related U.S. Application Data

[63] Continuation-in-part of application No. 08/446,503, May 22, 1995, Pat. No. 5,762,066
[60] Provisional application No. 60/000,813, Jun. 23, 1995.
[51] Int. Cl.[6] ........................................ A61B 8/00
[52] U.S. Cl. .................. 600/371; 600/439; 600/454; 601/2
[58] Field of Search ................. 128/660.03, 661.01, 128/661.08–661.09, 638; 601/2–4; 600/439, 411, 427, 447, 454, 455, 371

[56] References Cited

U.S. PATENT DOCUMENTS

| | | | |
|---|---|---|---|
| 4,905,672 | 3/1990 | Schwarze et al. | 601/4 |
| 4,938,217 | 7/1990 | Lele | 601/3 |
| 5,178,135 | 1/1993 | Uchiyama et al. | 128/660.03 |
| 5,233,994 | 8/1993 | Shmulewitz | 601/2 |
| 5,630,837 | 5/1997 | Crowley | 128/660.03 |

*Primary Examiner*—Ruth S. Smith
*Attorney, Agent, or Firm*—Barnes & Thornburg

[57] ABSTRACT

Methods and apparatus for the remote coagulation of blood using high-intensity focused ultrasound (HIFU) are provided. A remote hemostasis method comprises identifying a site of internal bleeding and focusing therapeutic ultrasound energy on the site, the energy being focused through an intervening tissue. An apparatus for producing remote hemostasis comprises a focused therapeutic ultrasound radiating surface and a sensor for identifying a site of internal bleeding, with a registration means coupled to the radiating surface and the sensor to bring a focal target and the bleeding site into alignment. The sensor generally comprises a Doppler imaging display. Hemostasis enhancing agents may be introduced to the site for actuation by the ultrasound energy.

19 Claims, 4 Drawing Sheets

DEVICES FOR PROVIDING ACOUSTIC HEMOSTASIS

This application is a regular utility application claiming the benefit of the filing date of Provisional U.S.patent application Ser. No, 60/000,813, filed Jun. 23, 1995. This application is also a Continuation-In-Part of U.S. Ser. No. 08/446,503, filed May 22, 1995, now U.S. Pat. No. 5,762,066.

BACKGROUND OF THE INVENTION

1. Field of the Invention

The present invention relates generally to the remote application of therapeutic radiated energy. In particular, the present invention provides a method for applying High Intensity Focused Ultrasound to reduce internal bleeding.

The use of ultrasound for imaging and diagnosis of disease is well known in the medical field. Ultrasound imaging generally relies on differences in the reflection of high frequency acoustic waves by organs and soft tissues. Ultrasound waves, when applied at power levels required for imaging, have been found to be free from the deleterious side effects associated with many other forms of radiated energy, such as X-rays, microwaves, and other electromagnetic fields. Hence, ultrasound imaging systems have a distinct safety advantage over other known imaging modalities.

Generally, imaging ultrasound waves are radiated from a transducer which also senses the reflections. Imaging ultrasound transducers often make use of multiple radiating and/or receiving surfaces. For example, modern ultrasound probes often use precise timing control over a series of active surface regions, referred to as a phased array, to control the radiation direction and to sense the source of reflections. Ultrasound imaging systems having multiple transducer surface regions have found particular use in Doppler measurements of internal blood flows.

Ultrasound Doppler imaging systems make use of multiple ultrasound pulses to non-invasively monitor internal movements. Doppler imaging typically relies on the frequency shift of acoustic reflections from moving matter, and also on the change in position of discrete masses between pulses. Doppler colorflow imaging indicates relative speeds of motion by assigning a range of false colors for the measured speeds. Ultrasound Doppler systems may scan a single sector of tissue, or may scan in multiple orientations to provide three-dimensional imaging. Array transducers facilitate Doppler imaging by providing electronic scanning through control of the phase of excitation provided to the discrete regions of the array.

Although ultrasound imaging is noted for its safety, ultrasound energy applied at higher power densities can have significant physiological effects on tissues. These physiological effects may result from either thermal or mechanical effects of ultrasound energy. Thermal effects of ultrasound include localized heating, hyperthermia, and ablation of tissue (with relatively low energy levels), and even rapid high temperature searing. Mechanical effects include breaking-up of solid objects, liquefaction of tissues, and cavitation.

These effects of high power ultrasound can occur adjacent to the ultrasound radiating surface, or they may be produced at a distance from the radiating surface by focusing of the ultrasonic waves at a target region within the tissue. For example, lithotriptors use a large external radiating surface to focus short bursts of ultrasound energy as shock waves inside a patient body, thereby mechanically fragmenting kidney stones. Clearly, the ultrasound energy must be focused on a target region which is very small relative to the transmitting surface to avoid affecting the intermediate tissue.

The use of High Intensity Focused Ultrasound (herein referred to as "HIFU") has previously been proposed as a therapy for a number of diseases which manifest themselves in a localized or "focal" manner. Focal diseases for which HIFU has been suggested include, for example, neoplastic and other diseases of or in the brain, breast, liver, and prostate. Although surgical procedures have been developed for these diseases, HIFU therapy potentially offers a non-invasive or minimally invasive alternative, thereby inflicting much less trauma on the patient, and promoting faster healing. For example, HIFU therapy is now available as a treatment for Benign Prostatic Hyperplasia, allowing the remote ablation of hyperplastic tissue without physical penetration of the urethra and prostate, thus reducing the risk of infection.

U.S. application Ser. No. 08/446,503, the full disclosure of which is herein incorporated by reference, describes an exemplary HIFU system and method for the treatment of BPH and other focal diseases. This exemplary HIFU system includes a probe housing containing a multifaceted therapeutic transducer member and a servo system for aiming the transducer member within the probe. The transducer member has a plurality of radiating surfaces having different focal lengths and different radial orientations. Power is transmitted to alternative radiating surfaces to select a target depth. Additionally, an independent inner region of each radiating surface allows further variation in the target depth by manipulating the inner region's power supply phase relative to the surrounding outer region, the inner and outer regions acting as a simple phased array. An imaging transducer is also carried on the transducer member, allowing a single servo system to select the focal depth, aim the therapeutic surface, and scan the imaging transducer.

Although the above described HIFU system and probe have proven highly effective as a tool for applying HIFU therapy to focal diseases, the HIFU methods and systems proposed to date suffer from certain limitations. Specifically, HIFU treatments have generally relied only on the thermal and mechanical effects of ultrasound energy on fixed tissues and structures. The potential application of therapeutic ultrasound energy on body fluids, particularly for the coagulation of blood to control internal bleeding, has not previously been explored.

One of the most common causes of the death of trauma victims, both military and civilian, is internal bleeding. Broadscale internal bleeding is difficult to detect, has few well-recognizable symptoms, and can lead to death within a time ranging between minutes and several days. Blunt trauma often leads to hemoperitoneum from a rupture of the blood supply system of the abdominal organs and tissues, thus causing leakage of blood into the abdominal cavity and surrounding tissues. The organs most commonly injured include the liver, spleen, and kidneys. The survival rates from trauma victims with hemoperitoneum has been found to increase dramatically when proper care is provided soon after the injury.

The survival rate of trauma victims who survive long enough to receive state-of-the-art medical care at a major medical facility is relatively good. Once at such a facility, intra-abdominal fluid is often detected using Diagnostic Peritoneal Lavage (DPL). DPL is an invasive procedure having a complication rate of as high as 5%, typically from bowel or bladder perforation. Although ultrasound Doppler imaging offers a non-invasive diagnostic alternative, invasive therapies are generally required after diagnosis to control any significant internal bleeding.

Unfortunately, facilities capable of invasive surgical procedures, including DPL and abdominal surgery, are often a considerable distance from the injury site, requiring considerable transportation time. Additional time after arrival at a surgical facility is required for preparation of the patient, staff, and medical equipment for surgery. Meanwhile, the internal bleeding continues, as well as the associated risk to the trauma victim.

For these reasons, it would be desirable to provide methods and system for identifying, targeting, and controlling of internal bleeding, preferably without the damage to surrounding or intervening tissue associated with surgical intervention. Preferably, such methods would provide hemostasis sufficient for the transport of patients to a critical care facility, where more conventional surgical and diagnostic techniques are available. Ideally, these methods and systems for production of coagulation would be suitable for emergency rooms, local clinics, and even paramedics in the field. It would be best if such methods and systems could make use of the advances in imaging and therapeutic ultrasound technologies which have previously been applied to focal diseases.

2. Description of the Background Art

U.S. Pat. No. 5,322,055 describes an ultrasonic clamp which coagulates tissues within a scissor-like jaw as it cuts. U.S. Pat. No. 5,013,312 describes an ultrasonic scalpel having an integral bipolar electrode to coagulate as it cuts.

U.S. Pat. No. 5,207,672 describes the use of laser energy to cause coagulative necrosis of compressed prostatic tissue. U.S. Pat. No. 5,269,778 describes the use of a variable pulse width laser to penetrate tissue and effect deep coagulation.

U.S. Pat. No. 5,052,395 describes an ultrasonic pulse Doppler cardiac monitor which measures blood velocity. U.S. Pat. No. 5,152,294 describes a three-dimensional ultrasonic scanner. U.S. Pat. No. 5,186,175 describes a two-dimensional ultrasonic diagnostic array. U.S. Pat. Nos. 5,379,642, 5,255,682, 4,945,915, 4,155,260, and 5,050,588 are generally relevant.

C. Delon-Martin et al., *Venous Thrombosis Generation by Means High-Intensity Focused Ultrasound*, Ultrasound in Medicine and Biology, 21:113 (1995) describes a HIFU for sclerotherapy of superficial varicose veins. Vein walls were specifically targeted for thermal ultrasonic therapy, leading to temporary vein occlusion.

V. Zurinski et al., *Real-Time Sonography with the Linear Array Scanner Multison 400*, Electromedica, 46, No. 4 (1978); R. D. Selbie et al., *The Aberdeen Phased Array: A Real-Time Ultrasonic Scanner with Dynamic Focus*, Medical and Biological Engineering and Computing, 18:335 (May 1980); O. T. von Ramm et al., *Thaumascan: Design Considerations and Performance Characteristics*, Ultrasound in Medicine, 1:373 (October 1974); D. Latham King, *Real-Time Cross-Sectional Ultrasonic Imaging of the Heart Using a Linear Array Multi-Element Transducer*, The Journal of Clinical Ultrasound, 1:196 (1973) are also generally relevant.

SUMMARY OF THE INVENTION

The present invention promotes the remote coagulation of blood using high-intensity focused ultrasound (HIFU). In particular, the present invention provides methods and devices for identifying a site of internal bleeding, and focusing therapeutic ultrasound energy through an intervening tissue and onto the bleeding site, so as to remotely provide hemostasis. Such systems and methods allow the diagnosis and stabilization of trauma victims suffering hemoperitoneum without resorting to invasive surgical procedures. Advantageously, the remote hemostasis of the present invention may be used as a complete therapy, or may alternatively be used to buy time for the patient to reach and receive conventional treatment in a critical care facility.

In a first aspect, the method of the present invention comprises identifying a site of internal bleeding, and focusing therapeutic ultrasound energy on the site. The energy is transmitted from a radiating surface and passes through an intervening tissue. The focused energy coagulates blood adjacent to the internal bleeding site, thereby providing hemostasis.

As used herein "hemostasis" is defined as a temporary or permanent reduction or cessation of the release of blood from the circulatory system, tissues, and organs.

Preferably, the identifying step comprises Doppler imaging a section of the patient body with a pulsed ultrasound transducer, typically using colorflow imaging techniques. Additionally, the identifying step preferably comprises elasticity imaging. As more fully described in U.S. Pat. No. 5,178,147, the full disclosure of which is incorporated herein by reference, elasticity imaging is performed by locally displacing tissue and monitoring the tissue displacement. Elasticity imaging is particularly well-suited or the identification of stiff coagulated regions and unconstrained liquids such as freestanding blood. Alternatively, a contrast agent may be introduced into the blood stream and an X-ray or ultrasound angiogram made to identify the internal bleeding site. Optionally, identification relies on sensing and isolating the acoustic or other vibrational signature of a vascular breach.

In a second aspect, the present invention provides a method comprising identifying a site of internal bleeding, targeting a region adjacent to the site for therapy, and focusing therapeutic ultrasound energy on a target within the therapy region. The ultrasound energy is again emitted from a radiating surface, and passes through an intervening tissue on its way to the target. Generally, an appropriate target depth is also selected. Preferably, the radiating surface and an ultrasound imaging transducer array are carried within a single housing, allowing the device to be easily aimed towards the internal bleeding site by moving the housing over the patient's skin in a "point-and-shoot" mode.

The focusing step of the method of the present invention generally comprises coagulating blood at the target. In connection with the present invention, it has been discovered that such coagulation is apparently the result of at least three separate mechanisms. First, heating has been observed to cause thrombosis, even at relatively low levels above body temperature. Second, mechanical streaming of blood caused by the ultrasound energy, and the impact of that blood with vessel walls and other obstructions, has been observed to cause the production of thrombi. Third, HIFU typically produces cavitation in the focal zone. Such cavitation can result in the production of free radicals as a chemical by-product. Such free radicals have been associated with the production of thrombi. Finally, there are reasons to believe that other chemical changes in the blood caused by ultrasound can also be contributory to the production of thrombi.

In certain cases, such as vascular breaches in smaller blood vessels, hemostasis is provided by coagulating blood so as to form a plug within the vessel. Preferably, the therapy volume extends upstream of the vascular breach along the blood vessel, so that the plug occludes the vessel and reduces the release of blood. Alternatively, hemostasis may be achieved by cauterizing tissue, particularly by selecting a therapy region which encompasses an organ fracture. In certain cases, the ultrasound energy may be used to weld tissues at the target, analogous to the ultrasonic cauterization of vessels produced by mechanical ultrasonic clamps.

In yet another aspect, the present invention provides a method for producing remote hemostasis comprising identifying a site of internal bleeding, and introducing an ultrasound hemostasis enhancement agent to the site. Therapeutic ultrasound energy is then focused from a radiating surface to activate the hemostasis agent adjacent to the site, the energy passing through an intervening tissue. Optionally, the hemostasis agent foams under ultrasound energy, so as to occlude a vascular breach. Suitable foaming hemostasis agents includes perfluorocarbons, particularly those having boiling temperatures between 40° C. and 80° C. Alternatively, the hemostasis agent comprises an encapsulated thrombus-producing agent, typically being an element from the clotting cascade. The use of such hemostasis agents will be particularly advantageous for providing remote hemostasis to vascular breaches of major vessels, for example, in stabilizing a ruptured abdominal aneurysm without occluding the aorta.

An apparatus for producing remote hemostasis according to the present invention comprises a radiating surface which applies focused therapeutic ultrasound energy on a remote target, and a sensor for identifying a site of internal bleeding. A registration mechanism is coupled to the radiating surface and the sensor to align the target and the internal bleeding site. Therapy for internal bleeding is thereby provided without the need for invasive surgical procedures, even at remote locations where surgical facilities are not available.

Preferably, a mechanism is provided to allow variations in therapy depth by adjustments to the effective focal length of a radiating surface, thereby varying the distance between the radiating surface and the target. Ideally, the radiating surface is formed as a phased array, and the depth varying mechanism comprises a phase controller. A phased array comprising an annular array is particularly preferred, allowing simple and accurate variations in focal depths with a minimum amount of circuit complexity.

Optionally, the registration means comprises a mechanical linkage between the radiating surface and the sensor. The radiating surface and sensor may be affixed to a common structure to facilitate registration of the target. Nonetheless, one or more degrees of freedom are often provided between the sensor and radiating surface, for example, the variable therapy depth of a phased annular array radiating surface, or the linear and sector scan servo mechanisms which alter the radiating surface orientation after an imaging scan and before therapy is applied. Thus, in certain embodiments, the registration means comprises a position indication system coupled to the radiating surface and the sensor. Where the position indication system comprises a global positioning system providing the complete position and orientation of the radiating surface, the target may be registered to the site despite the lack of any mechanical linkage. Typically, a 3-D model of a portion of the patient body is assembled from the imaging data supplied to a processor by the sensor, and the target is then electronically registered to the 3-D model using data provided by the position indication system.

In another aspect, an apparatus for producing remote hemostasis according to the present invention comprises a pulsed ultrasound imaging transducer and an ultrasound radiating surface which focuses therapeutic energy at a target. A display is coupled to both the imaging transducer and to the radiating surface, so that the display indicates a relative position of the target and an internal bleeding site. Preferably, the radiating surface comprises a phased array to provide a variable therapy depth, while the display generally indicates any difference between the selected depth and the depth of the site.

Optionally, a structure carries the transducer and the radiating surface, and a translation of the structure relative to the site results in a repositioning of the site relative to the target on the display. Such a structure, typically comprising a housing, allows at least rough locating of the internal bleeding site by relocating or sliding the housing over the patient's skin. Optionally, precise positioning is provided by a servo mechanism supporting the radiating surface from the housing structure, or by electronic manipulation of the phased array. Alternatively, the remote hemostasis apparatus may be used as a "point-and-shoot" device, being aimed toward the target location by hand, focused to the target depth by manipulation of an annular array, and manually activated. Such a "point-and-shoot" device would be particularly advantageous for emergency medical personnel, including both civilian paramedics and military field medics.

Preferably, the display will provide a Doppler colorflow image, facilitating the identification of internal bleeding. Optionally, a tissue displacement mechanism is coupled to the imaging transducer, allowing the display to provide an elasticity image as described above. As well as providing indications of internal bleeding, such Doppler colorflow images and elasticity images will also facilitate the identification and mapping of coagulated and cauterized regions, thereby enhancing the therapy zone management of the apparatus. Optionally, a coagulation memory is coupled to the radiating surface and the display so that the display electronically indicates coagulated regions.

DETAILED DESCRIPTION OF THE SPECIFIC EMBODIMENTS

The present invention provides a high-intensity focused ultrasound (HIFU) system and methods for its use to provide remote hemostasis. The HIFU apparatus of the present invention will find a wide range of applications for the identification and targeting of internal bleeding. The present invention will have particular applications for aneurysms and other diseases of the vascular system. The apparatus and methods of the present invention will find further use in establishing hemostasis after an invasive surgery surgical procedure. Furthermore, hemostasis and cauterization provided by the present invention may be used to deny a supply of blood to certain diseased tissues, particularly tissues having hyperplastic diseases.

The present remote hemostasis apparatus and methods may be applied laparoscopically, using an intraluminal probe, minimally invasively, using an intracavity probe, or non-invasively, using an extracorporal probe. Although such systems and methods will thus have a wide range of applications, the present invention will find its greatest applications in the stabilization of the victims of blunt trauma, either prior to conventional invasive procedures, or instead of such procedures. The methods and apparatus of the present invention are particularly well-suited for medical and emergency personnel who do not have immediate access to extensive critical care health facilities.

Figure 1:
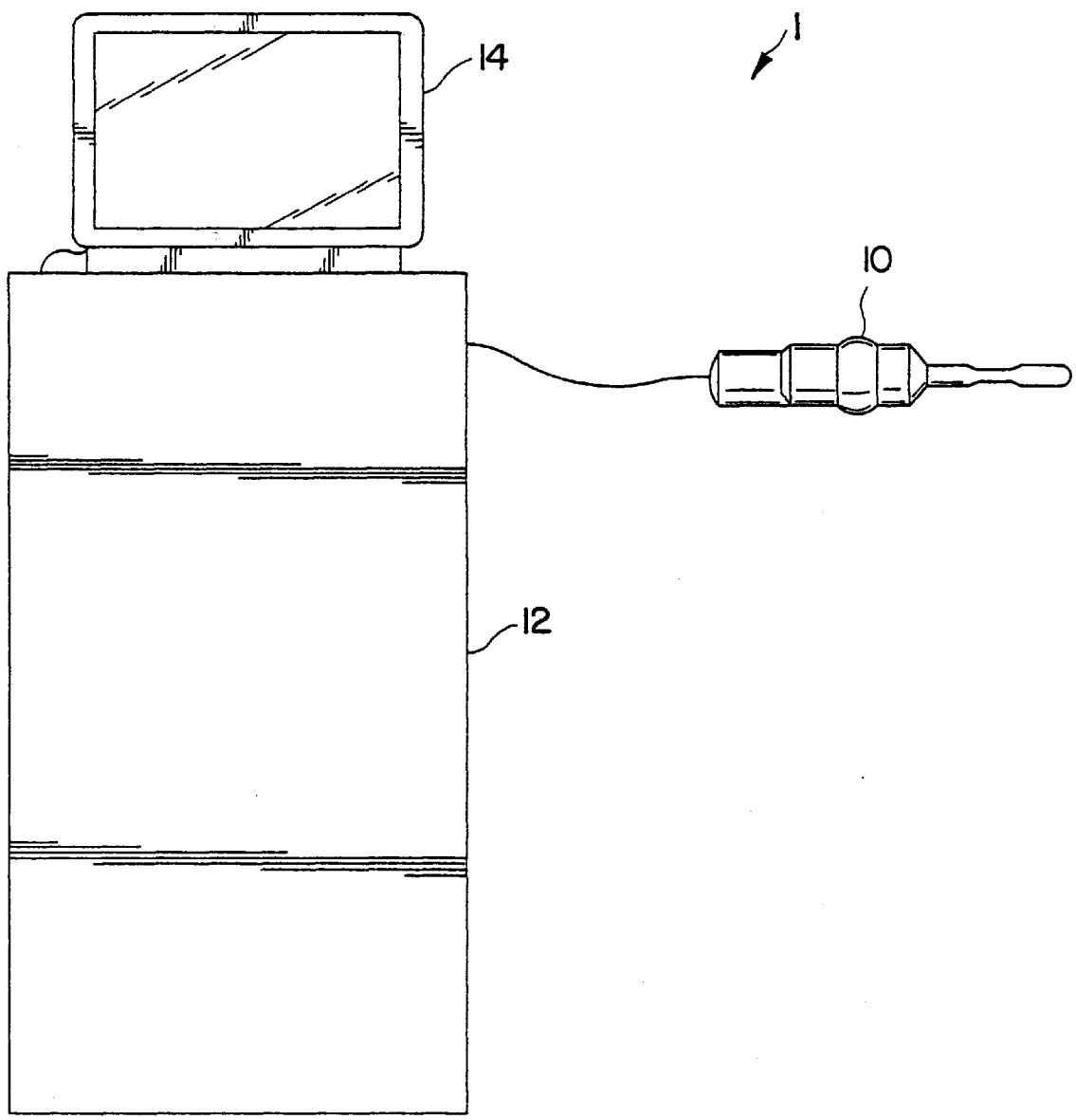
FIG. 1 illustrates a high-intensity focused ultrasound (HIFU) remote hemostasis apparatus according to the principals of the present invention.

Referring now to FIG. 1, the remote hemostasis system 1 includes a probe 10 and a controller 12. Controller 12 includes a display 14, which is used to image tissues, identify internal bleeding sites, and select zones of a patient body for therapy. Remote hemostasis system 1 is a specialized ultrasonic therapy system of the general type which is more fully described in application Ser. No. 08/446,503, the full disclosure of which has previously been incorporated herein by reference. The structure of the present system is also described in U.S. patent application Ser. No. 07/840,502, filed Feb. 21, 1992, and reproduced in PCT Patent Application No. PCT/US93/01551, published Sep. 2, 1993, the full disclosures of which are also incorporated herein by reference.

As more fully explained in the application Ser. No. 08/446,503, probe 10 is adapted for use as an intracavity probe, typically being used by positioning a patient on a treatment table and transrectally inserting and positioning the treatment probe. A transducer disposed within the probe housing images a tissue using a linear and/or sector scanning movement of the transducer relative to the housing. The operator graphically selects a therapy volume, and also inputs treatment parameters. The controller automatically linearly and angularly positions the transducer so that the active surface is focused at the target tissue. The controller then activates the focused radiating surface of the transducer, applying therapeutic ultrasound energy to a target within the therapy zone.

Figure 2:
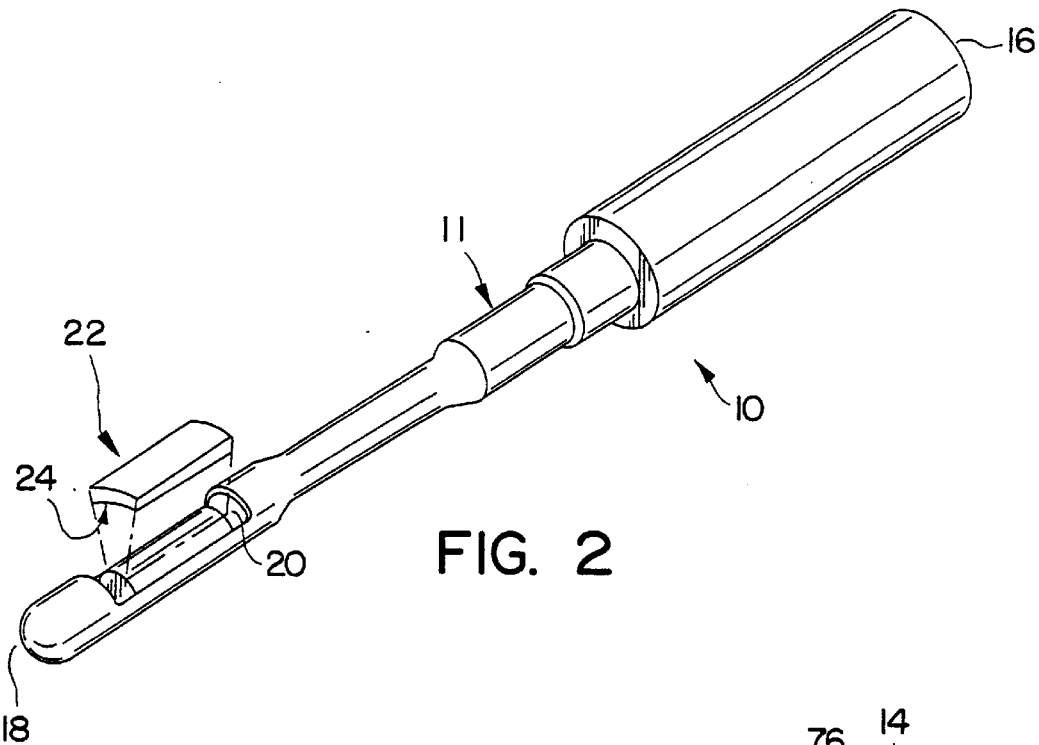
FIG. 2 illustrates a HIFU probe for use with the remote hemostasis apparatus of FIG. 1.

Referring now to FIG. 2, probe 10 includes a probe housing 11 having a proximal end 16, a distal end 18 and an acoustic window 20. The probe housing is shown without a membrane over window 20 for clarity. The distal portion of housing 10 contains a transducer member having back-to-back active surfaces with focal geometries at a first and a second distance from the probe housing 11, respectively (see FIG. 5). By rotating the transducer member within the housing and energizing the radiating surfaces independently, probe 10 is capable of applying HIFU therapy focused at a first distance 22 from housing 11 and also at a second distance 24 from housing 11. Generally, the actual first and second target volumes associated with these distances will at least be adjacent, and will preferably overlap, so that ultrasonic therapy can be applied to coagulate blood and/or cauterize tissues which lie throughout the volume between first distance 22 and second distance 24. Additionally, one or both of the back-to-back radiating surfaces comprise annular arrays, allowing electronic adjustments of the therapy distances, as described hereinbelow.

Figure 3:
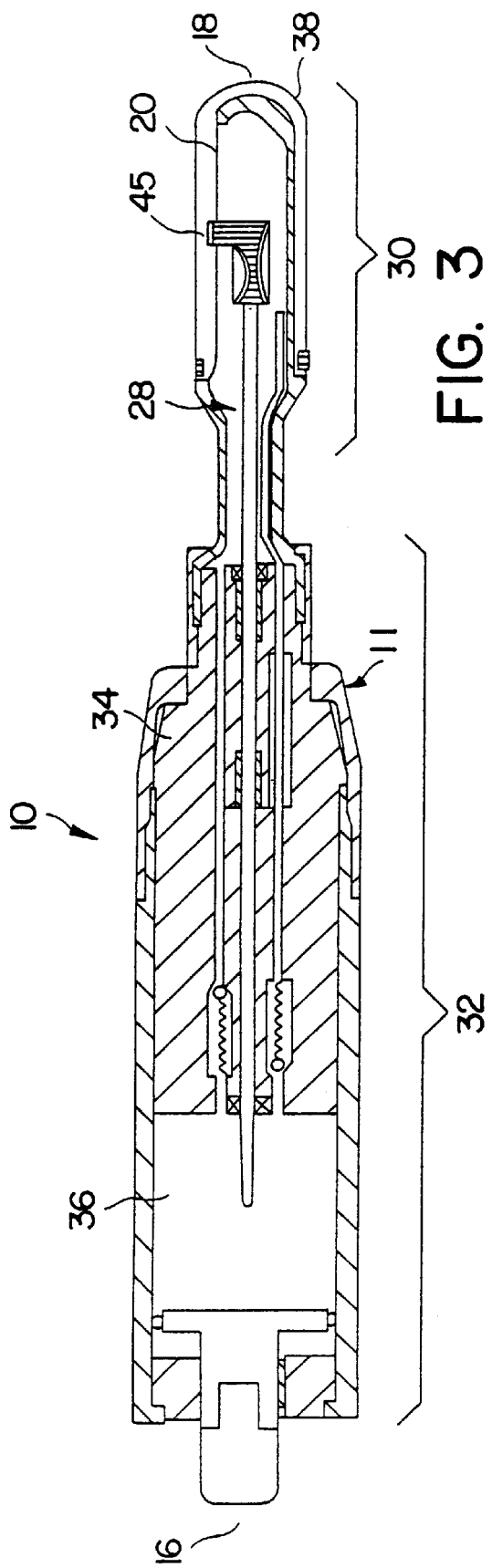
FIG. 3 is a cross-section of the HIFU probe of FIG. 2.

Referring now to FIG. 3, probe housing 11 contains a transducer member 28 featuring two back-to-back therapeutic ultrasound focusing radiating surfaces having different focal geometries. Probe housing 11 broadly includes a transducer region 30 near distal end 18 and a handle region 32 near proximal end 16. Probe housing 11 may be formed from polyurethane, ABS plastic, or the like.

Transducer member 28 is disposed within an interior volume defined by transducer region 30, but does not contact probe housing 11 in the transducer region, being cantilevered from the handle region 32. Transducer member 28 is thus free to both rotate about the axis of transducer region 30, and to translate axially. Window 20 provides passage for ultrasonic energy within a range of axial and angular positions of the radiating surfaces of transducer member 28, as seen in FIG. 2. Disposed over the distal end 18 of transducer region 30 is an acoustic membrane 38.

Contained within handle region 32 of housing 11 are a transducer positioning mechanism 34 and a reservoir 36. Positioning mechanism 34 provides linear and sector scanning motion to transducer member 28 relative to housing 11, and also provides position feedback to controller 12 (see FIG. 1). Positioning mechanism 34 allows aiming of the radiating surfaces towards the internal bleeding site, selects between the back-to-back radiating surfaces, and also mechanically scans an ultrasonic imaging transducer array 45 attached to transducer member 28. An exemplary positioning mechanism was described in application Ser. No. 07/840,502.

Figure 4:
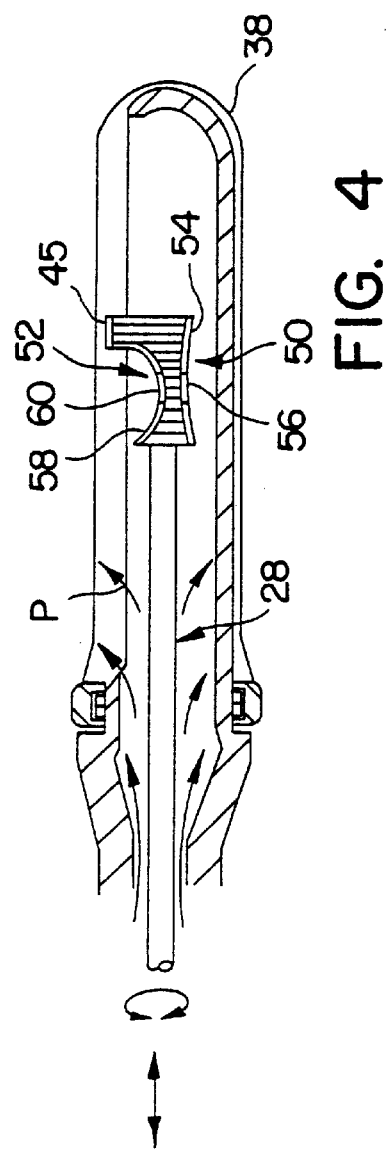
FIG. 4 is a cross-section of the distal end of the HIFU probe of FIG. 3, showing a membrane pressurization system which acts as a local tissue displacement mechanism for elasticity imaging.

Referring now to FIG. 4, transducer member 28 includes a first radiating surface 50 having a relatively long focal length and a second radiating surface 52 having a relatively short focal length as compared to the long focal length. First radiating surface 50, in turn, includes an inner region 56 and an outer region 54, while second radiating surface 52 similarly includes inner and outer regions 60, 58. This separation of first radiating surface 50 and second radiating surface 52 into inner and outer regions allows additional control over the therapy depth by varying the relative phase of power supplied to the inner and outer regions, first and second radiating surfaces 50, 52 acting as simple annular phased arrays. The use of annular phased arrays for controlling the depth of therapeutic ultrasound focusing is more fully explained in co-pending U.S. patent application Ser. No. 08/333,471, the full disclosure of which is herein incorporated by reference. Clearly, a larger number of regions provides additional flexibility in the focal depth.

The radiating surfaces of transducer member 28 are coupled to acoustic membrane 38 by a coupling fluid contained within transducer region 30 of probe housing 11. Acoustic membrane 38 is, in turn, coupled to the patient body by direct contact against tissue in the region of acoustic window 20. Optionally, transducer region 30 is inserted transrectally, transvaginally, transesophageally, or the like. Alternatively, coupling membrane 38 is held against the patient's skin, either manually or using a table clamp attached to the probe, as known in the art. Such extracorporal coupling of the radiating surface to the tissue of the patient body allows aiming of the radiating surfaces by repositioning probe 10 against a different region of the patient's skin, ideally by sliding acoustic membrane 38 against the skin. Once probe 10 is roughly in position, the servo mechanisms of transducer positioning mechanism 34 may be used to precisely aim the radiating surfaces 50, 52. Alternatively, a radiating surface comprising a two-dimensional phased array would allow electronic aiming and focusing, analogous to the electronic variation in therapy depth provided by an annular array.

Acoustic membrane 38 may conveniently be integrated into a local tissue displacement mechanism for elasticity imaging. While transducer region 30 is held in coupling contact with the patient body, coupling fluid pressure P may be varied in a controlled fashion to displace the tissue which is adjacent to ultrasound transducer array 45. Acoustic membrane 38 ideally comprises an inelastic, non-distensible, thin membrane as described in application Ser. No. 08/446,503, typically being formed of PET, polyamide, or polyethylene, preferably being less than one wavelength of ultrasonic energy in thickness. Preferably, the tissue displacement mechanism operates at a regular interval, usually having a frequency between 1 and 50 Hz.

Figure 5:
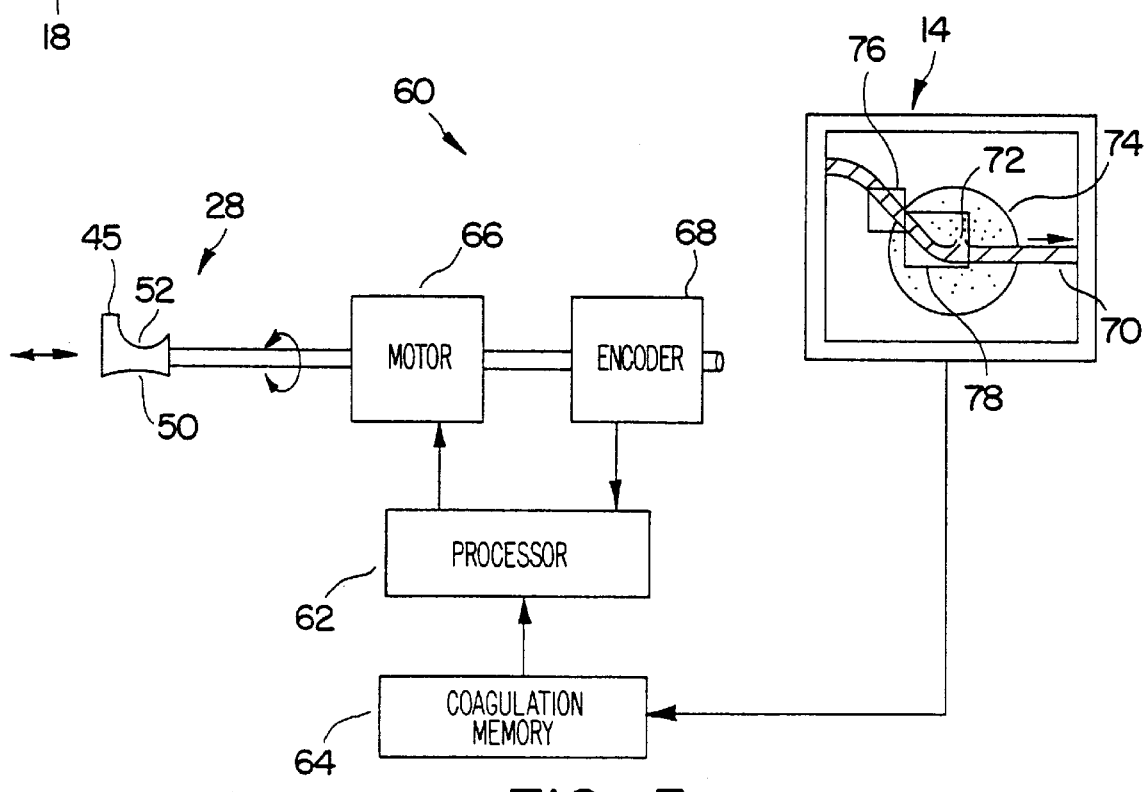
FIG. 5 illustrates a control diagram for the remote hemostasis apparatus of FIG. 1.

Referring now to FIG. 5, a registration system 60 comprises a processor 62, a memory 64, and display 14. Positioning mechanism 34 (shown in FIG. 3) is located in the probe handle, and includes a rotational positioning motor 66 and a rotational position indicator 68. As described above, imaging transducer 45 provides an image of a portion of a patient body having an internal bleeding site, typically using pulsed Doppler colorflow imaging, elasticity imaging, an angiogram, or the like. Display 14 provides an image of the internal bleeding site.

As shown in FIG. 5, a blood vessel 70 having a vascular breach 72 has released blood into the abdominal cavity. The blood forms a low pressure pool 74, which has been identified using display 14. Typically, imaging transducer 45 sweeps a section of the patient body to produce the image, either mechanically sweeping using motor 66, or electronically sweeping by use of a phased array.

The operator selects a treatment volume, for example, by manipulation of a trackball, a mouse, or the like. As shown, a deep therapy volume 76 and a shallow therapy volume 78 have been defined. Such therapy volumes, targeting both the blood within the vessel and the vessel wall itself, promotes the formation of a plug to occlude the vessel and prevent blood leaking from vascular breach 72.

Imaging transducer 45 and radiating surfaces 50, 52 are supported on transducer member 28. This mechanical connection facilitates the aligning of a selected treatment target within a therapy volume to the internal bleeding site. Nonetheless, transducer member 28 will rotate between imaging and therapy, particularly when therapy is provided by radiating surface 50. Thus, processor 62 manipulates transducer member 28 using rotational motor 68, and receives feedback from position indicator 68 to register the treatment target to the therapy zone adjacent to the internal bleeding site. Preferably, as individual targets are coagulated, coagulation memory 64 maps that information on display 14, allowing efficient therapy zone management.

Figure 6:
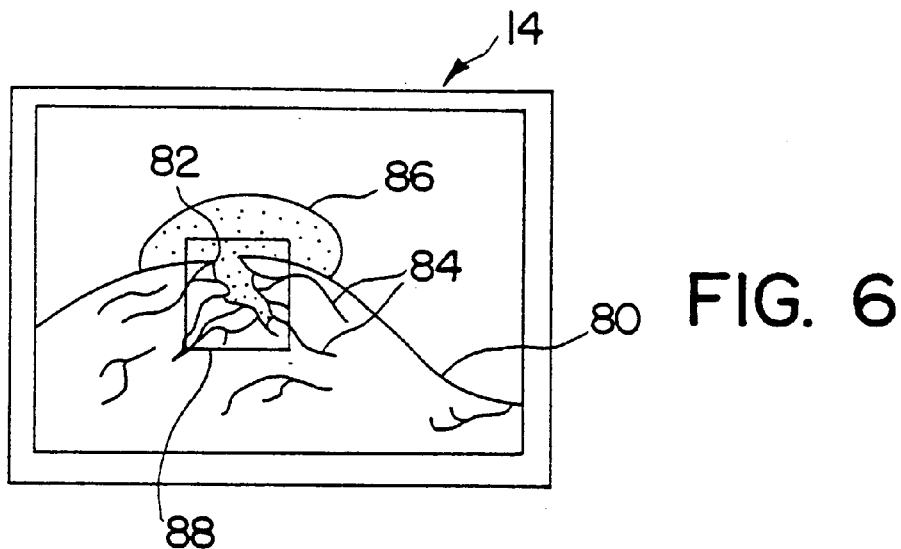
FIG. 6 illustrates a therapy zone appropriate for providing hemostasis of an organ fracture using the remote hemostasis apparatus of FIG. 1.

Referring now to FIG. 6, an organ 80 having an organ fracture 82 oozes blood from a large number of small vessels 84, resulting in a pool of blood 86 within the abdominal cavity. A therapy volume 88 is selected which not only coagulates blood, but also cauterizes the soft tissue of the organ in the area adjacent to the organ fracture. Thus, perfuse organs such as the liver and kidneys may be selectively cauterized to provide acoustic hemostasis without resorting to occlusion of a multiplicity of individual blood vessels.

Figure 7A:
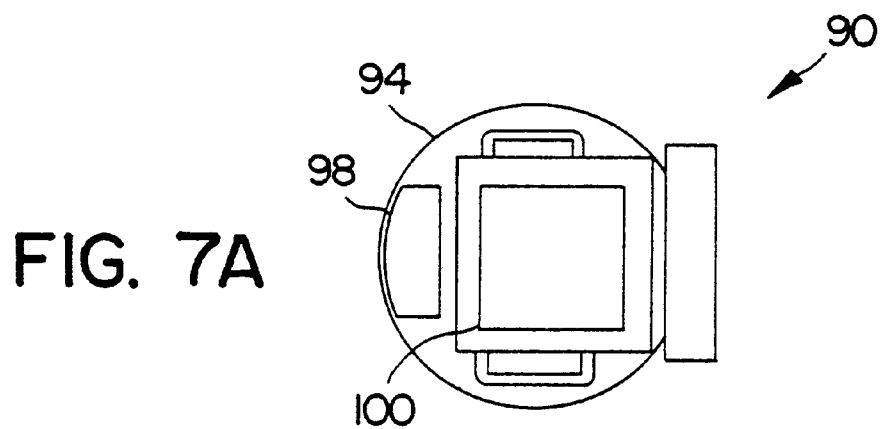
FIGS. 7A–C illustrate a self-contained point-and-shoot remote hemostasis apparatus according to the principles of the present invention.
Figure 7B:
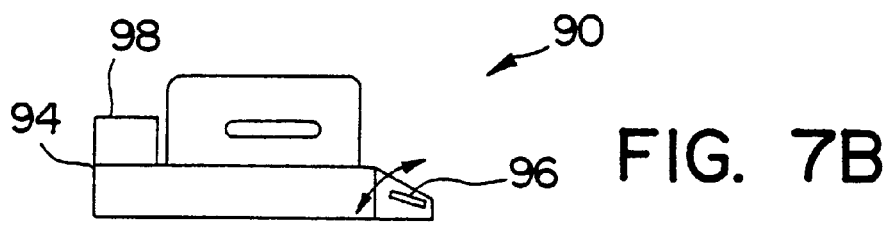
Figure 7C:
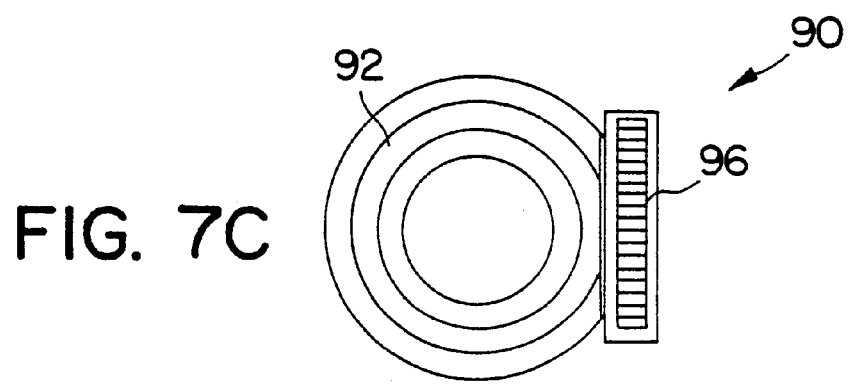

Referring now to FIGS. 7A–C, a point-and-shoot remote hemostasis probe 90 comprises a radiating surface in the form of an annular array 92. Annular array 90 applies therapies at depths ranging up to 3/2 the array aperture, the aperture typically being between two and ten inches. Annular array 92 is carried by a housing 94, which also carries a mechanically oscillating linear imaging transducer array 96. The imaging transducer and a global positioning system 98 provide information to a processor, which assembles a 3-D model of an internal region of a patent body. The model is displayed in real time on a screen 100, with the model orientation updated to reflect movement of probe 90 from data supplied by global positioning system 98.

Point-and-shoot probe 90 is particularly advantageous for field medical treatment, allowing a paramedic to identify a site of internal bleeding, position the probe to target the site, select a proper therapy depth, and apply therapy to provide hemostasis before transporting the patient.

Although the specific embodiments have been described in detail, various alternatives, modifications, and equivalents, may be used. Thus, the above description should not be taken as limiting the scope of the invention, which is instead defined solely by the appended claims.

What is claimed is:

1. An apparatus for producing remote hemostasis comprising:
    a radiating surface which applies focused therapeutic ultrasound energy to a target volume, the target volume being separated from the radiating surface by a therapy depth to produce remote hemostasis;
    a sensor which identifies a site of internal bleeding; and
    a registration mechanism coupled to the sensor and the radiating surface to align the target volume and the site.

2. A remote hemostasis apparatus as claimed in claim 1, further comprising a therapy depth varying mechanism coupled to the radiating surface.

3. A remote hemostasis apparatus as claimed in claim 2, wherein the radiating surface comprises a phased array, and wherein the depth varying mechanism comprises a phase controller.

4. A remote hemostasis apparatus as claimed in claim 3, wherein the phased array comprises an annular array.

5. A remote hemostasis apparatus as claimed in claim 1, wherein the sensor comprises a pulsed ultrasound imaging transducer.

6. A remote hemostasis apparatus as claimed in claim 5, further comprising a display coupled to the imaging transducer for providing Doppler imaging of the site.

7. A remote hemostasis apparatus as claimed in claim 5, wherein the sensor further comprises a tissue displacement mechanism, the apparatus further comprising a elasticity imaging display coupled to the sensor.

8. A remote hemostasis apparatus as claimed in claim 1, further comprising a processor coupled to the sensor for isolating a vibrational signal of vascular breaches.

9. A remote hemostasis apparatus as claimed in claim 1, wherein the sensor comprises a display for providing angiographic imaging of the site.

10. A remote hemostasis apparatus as claimed in claim 1, wherein the registration mechanism comprises a mechanical linkage between the radiating surface and the sensor.

11. A remote hemostasis apparatus as claimed in 1, wherein the registration mechanism comprises a position indication system coupled to at least one of the radiating surface and the sensor.

12. An apparatus for producing remote hemostasis comprising:

a pulsed ultrasound imaging transducer which identifies a site of internal bleeding;

an ultrasound radiating surface which focuses therapeutic energy at a target volume to produce remote hemostasis; and a display coupled to the imaging transducer and to the radiating surface, the display indicating a relative position of the target volume and the internal bleeding site.

13. A remote hemostasis apparatus as claimed in claim 12, wherein the radiating surface comprises a phased array having a selectable therapy depth between the radiating surface and the target volume, and wherein the display indicates any difference in depth between the selected therapy depth and the site.

14. A remote hemostasis apparatus as claimed in claim 12, further comprising a structure which carries the imaging transducer and the radiating surface, wherein a translation of the structure relative to the site causes the display to indicate repositioning of the site relative to the target volume.

15. A remote hemostasis apparatus as claimed in claim 12, wherein the display comprises a display for providing Doppler colorflow imaging.

16. A remote hemostasis apparatus as claimed in claim 15 further comprising means for providing feedback on regions of coagulated blood.

17. A remote hemostasis apparatus as claimed in claim 12, further comprising a tissue displacement mechanism coupled to the imaging transducer, wherein the display provides an elasticity image.

18. A remote hemostasis apparatus as claimed in claim 17 further comprising means for providing feedback on both regions of coagulated blood and regions of cauterized tissue.

19. A remote hemostasis apparatus as claimed in claim 12, further comprising a coagulation memory coupled to the radiating surface and the display so that the display indicates coagulated regions.

\* \* \* \* \*